United States Patent [19]

Scheibel et al.

[11] Patent Number: 5,681,971
[45] Date of Patent: Oct. 28, 1997

[54] SYNTHESIS OF FATTY N-ALKYL AMIDES

[75] Inventors: Jeffrey John Scheibel, Cincinnati; Robert Edward Shumate, Hamilton, both of Ohio

[73] Assignee: The Procter & Gamble Company, Cincinnati, Ohio

[21] Appl. No.: 354,684

[22] Filed: Dec. 12, 1994

[51] Int. Cl.$^6$ .................................................. C07C 231/00
[52] U.S. Cl. ................................................ 554/69; 554/68
[58] Field of Search ............................................. 554/68, 69

[56] References Cited

U.S. PATENT DOCUMENTS 2,402,584  6/1946  Searle ........................................ 554/69
3,288,794  11/1966  Kuceski et al. ............................ 554/69

OTHER PUBLICATIONS

Kiyoshi Matsumoto et al., "Direct Aminolysis of Unactivated Esters at High–Pressure", Angew. Chemie Int. Ed. Engl., 25(6), (1986), pp. 565–566.

Spivack, "N–Acylated amino Acids as Surfactants", Surfactant Science Series, vol. 7, Part III, pp. 581–617.

*Primary Examiner*—José G. Dees
*Assistant Examiner*—Deborah D. Carr
*Attorney, Agent, or Firm*—Richard S. Echler, Sr.; Kim William Zerby; Jacobus C. Rasser

[57] ABSTRACT

Fatty N-alkyl amides are synthesized directly from glycerides (preferably triglycerides) and amines in the absence of a catalyst, and preferably without a solvent. The method provides for products suitable for use without further purification, preferably after separating the glycerol and amide products. The disclosed method is also useful for the synthesis of glycerol from glycerides and ammonia and/or primary amines.

2 Claims, No Drawings

SYNTHESIS OF FATTY N-ALKYL AMIDES

FIELD OF THE INVENTION

This invention relates to the direct formation of fatty N-alkyl amides in the absence of a catalyst, and preferably without a solvent. Employing readily available glyceride feed stock as a carboxylic acid ester source results in a low cost, high conversion method of synthesis of these amides. The present invention also relates to a process for readily preparing glycerol from triglyceride feed stock.

BACKGROUND OF THE INVENTION

The synthesis of ingredients for use in low unit cost consumer goods such as laundry detergents, fabric softeners, hard surface cleansers, and the like, is of considerable interest to manufacturers. Indeed, while formularies and patents are filled with listings of prospective ingredients for use in such products, the reality is that many such ingredients are simply too expensive for day-to-day use. This expense is often due either to the cost of the raw materials used to make such ingredients, or to the complex reaction and processing chemistry which is required in their manufacture. Accordingly, manufacturers have conducted a continuing search for both inexpensive raw materials and simple reaction sequences which can produce high performance, high value ingredients at the lowest possible cost.

The fatty N-alkyl amides comprise one class of chemicals whose functionality suggests their use, or use of derivatives thereof, as surfactants, fabric softeners, antistatic agents and the like. On the positive side, the fatty N-alkyl amides and their aforementioned derivatives are potentially obtainable from inexpensive raw materials. Unfortunately, the synthesis of certain fatty N-alkyl amides is somewhat complicated and can involve the use of solvents, with additional problems associated with recycle streams and the like. Problems can also arise with the formation of undesirable colored by-products. The present invention provides a simple method for the synthesis of fatty N-alkyl amides which may be used in laundry detergency compositions directly or converted by subsequent reactions to other useful materials.

The reaction sequence herein proceeds in yields (typically 97%, and higher) that allow for the use of this process as a low cost, high efficiency method for converting triglycerides to fatty N-alkyl amides and, importantly, results in products with minimal discoloration. The glycerol formed in the present process can also be easily removed from the reaction mixture and collected. The process thus allows the formulator to easily recover cleanly this valuable commodity.

The reactions preferably are conducted without added solvents, i.e., the reactants or products act as solvents, however, the user may wish at one or several steps to employ a suitable solvent to aid in the processing of the particular fatty N-alkyl amide. Hence, for many purposes the reaction product need not be extensively purified, which further improves the overall economics of the processes.

BACKGROUND ART

See *Surfactant Science Series*, Vol. 7, Part III, pg. 581–617, for general synthesis of amido acids. See Kiyoshi Matsumoto, et at., *Angew. Chemie Int. Ed. Engl.*, 25(6), pg 565–566 for review of syntheses of amides from esters and amines.

SUMMARY OF THE INVENTION

The present invention relates to a method for preparing fatty N-alkyl amides. Said method comprises the step of reacting, under anhydrous conditions that produce the fatty N-alkyl amide, glyceride and amine selected from the group consisting of ammonia, $C_1$–$C_6$ primary amine, and mixtures thereof.

The present invention preferably relates to a method for preparing fatty N-alkyl amides of the formula:

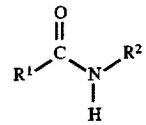

wherein $R^1$ is a $C_1$ or higher hydrocarbyl substituent and $R^2$ is hydrogen or a $C_{1-6}$ hydrocarbyl substituent. The method encompasses contacting an amine of the formula $R^2NH_2$ with a carboxylic acid ester glyceride, preferably a triglyceride of the formula:

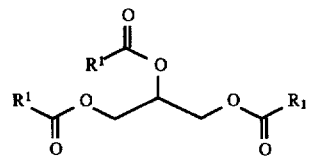

wherein each $R^1$ is the same or different $C_1$ or higher hydrocarbyl substituents. The reaction is preferably conducted at a temperature from about 70° C. to about 180° C. The high conversion of glyceride to amide results in a product mixture containing fatty N-alkyl amides, glycerol and any unreacted excess amine reactant (preferably little or no amine reactant). The absence of unreacted glyceride facilitates the isolation of the desired fatty N-alkyl amide (depending on the glyceride starting material, the amide formed may be a mixture of fatty N-alkyl amides) as well as the efficient recovery of the glycerol product.

The difference in physical properties between fatty N-alkyl amides and short chain ($C_{1-6}$) aliphatic amines allows for excess amine reactant to be removed directly from the reaction vessel by a means suitable to the nature of the $R^2$ moiety, and the recovered amine can then be purified, re-cycled or otherwise used by the formulator. Optionally, a suitable solvent can be introduced to facilitate work-up or isolation of the desired fatty N-alkyl amide. Solvents may also be used to aid in the separation of the glycerol product from the reaction matrix without affecting the fatty N-alkyl amide. Solvents can also be optionally used to induce final product crystallization or to otherwise facilitate further processing of the fatty N-alkyl amide.

Further, if desired, a suitable solvent may be included in the reaction step to aid in the initial contacting of reactants and manipulation of the reaction products, as well as to provide good mixing during the reaction as the triglyceride is depleted. This use of solvents may be desired for fatty N-alkyl amides of higher crystallinity such as those derived from hardened High Euricic Rapeseed oil. However, preferred methods herein use only low levels of solvent, and preferably are solventless processes.

All percentages, ratios and proportions herein are by weight, unless otherwise specified. All temperatures are in degrees Celsius (°C.) unless otherwise specified. All documents cited are, in relevant part, incorporated herein by reference.

DETAILED DESCRIPTION OF THE INVENTION

A reaction sequence (Sequence 1) for the synthesis of a preferred oleoyl amide is illustrated below. The reaction sequence as illustrated employs an oleoyl moiety for each $R^1$ hydrocarbyl substituent, and a methyl moiety for $R^2$, but is only by way of illustration and not limitation, as will be seen hereinafter.

Sequence 1

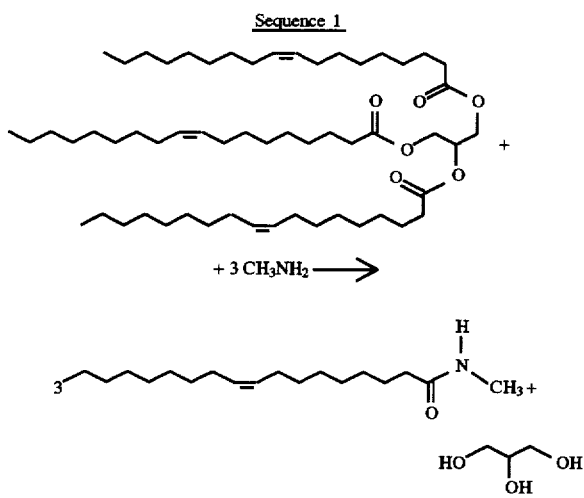

Glyceride Reactant - The glyceride used in the present invention can be any of the well-known fats and oils, such as those conventionally used as foodstuffs or as fatty acid sources. As such, they may be a mixture of mono-, di-, and triglycerides. Preferably, however, the glyceride reactant comprises a high level of triglyceride, and most preferably is essentially all triglyceride.

Non-limiting examples include: CRISCO® oil; palm oil; high oleoyl sunflower oil and high euricic rapeseed oil; palm kernel oil; corn oil; cottonseed oil; soybean oil; tallow; lard; canola oil; rapeseed oil; peanut oil; tung oil; olive oil; menhaden oil; coconut oil; castor oil; palm kernel oil; sunflower seed oil; palm stearine oil; and the corresponding "hardened", i.e., hydrogenated oils. If desired, low molecular weight or volatile material can be removed from the oils by steam-stripping, vacuum stripping, treatment with carbon or "bleaching earths" (diatomaceous earth), or cold tempering to further minimize the presence of malodorous by-products in the amido acids prepared by the present process.

The preferred glyceride reactants comprise $C_{6-24}$ acid esters, more preferably unsaturated acid esters such as oleic acid. Preferred triglycerides of the above formula have as the $R^1$ hydrocarbyl substituent chains selected from the group consisting of $C_{6-24}$ alkyl, $C_{6-24}$ branched alkyl, $C_{6-24}$ alkenyl, $C_{6-24}$ branched alkenyl, and mixtures thereof. More preferred are $C_{9-17}$ alkyl, $C_{9-17}$ branched alkyl, $C_{9-17}$ alkenyl, $C_{9-17}$ branched alkenyl, and mixtures thereof.

The preferred triglyceride contains at least 40% unsaturated chains, more preferably at least 70% unsaturated chains as the $R^1$ hydrocarbyl substituent. Oleoyl is the most preferred unsaturated chain as the $R^1$ hydrocarbyl substituent. The present invention allows the formulator to optionally hydrogenate the triglyceride hydrocarbyl substituents to a desired degree of un-saturation either before or after the reaction without loss of desired fatty N-alkyl amide profile. In some instances hydrogenation of the crude reaction mixture may facilitate the further processing or isolation of the desired fatty N-alkyl amide or range of fatty N-alkyl amide.

Amine Reactant - The amine used in the present invention can have as the $R^2$ hydrocarbyl substituent any $C_{1-6}$ linear alkyl, $C_{1-6}$ branched alkyl, $C_{1-6}$ linear alkenyl or $C_{1-6}$ branch alkenyl, with the $C_6$ amines including those moieties comprising six carbons in the length of the longest alkyl chain exclusive of branching. Non-limiting examples include methyl, ethyl, propyl, butyl, pentyl, hexyl, isopentyl, neopentyl, isobutyl, isopropyl, 5,5-dimethylhexyl, 2-propenyl, 2-butenyl, 2-hexenyl, 3-butenyl, 2,4-hexadienyl and 3-methyl-2-butenyl. Preferably the $R^2$ hydrocarbyl substituent is methyl or ethyl.

Optional Solvents - Solvents may be optionally used to aid in the processing of the final fatty N-alkyl amide products, for example, as an aid in crystalization or for the purpose of removing any excess amine reactant. Solvents may also be used in the reaction step to provide for increased efficiency of mixing when the amido acid forming reaction is carried out at lower temperatures which results in reaction solutions of increased viscosity. Glycerol may be added as a solvent at the start of a reaction sequence if desired to assist mixing.

However, preferred methods of the present invention are "solventless", which as used herein means that the glyceride and amine reactants are reacted under conditions wherein no materials other than reactants (i.e., glyceride and amine) or reaction products are present. This allows for the introduction of glycerol and/or amide into the process prior to the reaction step to assist, for example, in solubilization of the reactants.

Preferably, the present invention reactions are conducted using less than 10% solvent, more preferably less than 5% solvent, and most preferably are solventless.

Reaction Conditions - The reaction conditions of the present invention process may be as follows.

The reaction is conducted under anhydrous conditions, which as used herein means that the reactants are substantially free of water so as to avoid an unacceptably high level of ester hydrolysis during the reaction process resulting in significant reduction in amide yield. Thus, low levels of water can be tolerated as a minor component of the reactants (preferably in total for the reaction at a level less than 0.1% water). Preferably, however, the reactants comprise less than about 0.1% water, and in certain circumstances is desirable for the reactants to have been through a prior drying step to remove all but trace levels of water from the process.

The commercially available glyceride feed stocks and amine reagents are preferably selected so as to be sufficiently anhydrous to preclude the need for drying prior to reacting. Other sources of water are excluded, for example, methyl amine gas is used in the preparation of fatty N-methyl amides and not commercially available or commonly encountered aqueous solutions of methyl amine. Water is not a suitable solvent.

Any air in the system during the amidation step may cause darkening of the reaction mixture. Consequently, an inert gas (nitrogen is convenient) is preferably sparged through the glyceride prior to addition of the amine reactant. The reaction is preferably conducted in the melt. The reaction may be conducted by either a continuous or a batch process method.

Preferably for triglyceride reactants a minimum of three equivalents of the amine reactant is contacted with one equivalent of triglyceride reactant at a temperature from 70° C. to about 180° C. with efficient mixing. However, due to the slower reaction rates of some triglyceride/amine reactant mixtures, the formulator may wish to use a quantity of the amine reactant in excess of the stoichiometric amount. Especially in cases where the amine reactant is a gas at STP or a highly volatile liquid, then saturation of the reaction mixture may be necessary.

In the case of gases, a liquefaction step may be used to obtain the desired quantity of amine reactant followed by transfer to the reactor by suitable means, for example, by nitrogen pressurization or by re-expansion of the amine reactant into the evacuated head space of the reaction vessel. Similarly, the minimization of side reactions of the process of the present invention allows, when conventional triglycerides are employed, for the gradual addition of the amine reactant. Hence, an inefficient excess of the amine reactant need not be present at the beginning of the reaction but instead can be slowly metered into the reaction at a rate determined by the formulator. This gradual addition method is especially advantageous when there is a liquid/vapor phase equilibrium controlling the mount of amine reactant present in solution. Especially in cases where the pressure limit of a reaction vessel precludes the addition of all of the amine reactant necessary to afford complete triglyceride conversion, additional gaseous amine reactant can be directly added to the reaction vapor phase as needed.

The course of the reaction as well as the length of reaction time is typically determined by gas chromatograph, I.R. spectroscopy, or by other suitable means used by those skilled in the art usually by monitoring the uptake of glyceride and the formation of such products as the fatty N-alkyl amides and glycerol.

Product work-up - The product work-up can be accomplished in a manner suitable to the physical and bulk properties of the final fatty N-alkyl amide and the degree to which the reaction has been allowed to progress. The relative mount of amine reactant present in the crude reaction mixture will depend upon the excess used by the formulator and will effect the manner and the degree with which isolation and work-up is necessary. In the case where reaction conditions dictate the use of a large excess of a volatile amine such as methyl amine, careful cooling and venting of the reaction vessel followed by vacuum stripping of the system may be necessary.

Removal of glycerol - The present invention reaction process allows for the recovery of the glycerol product, either after subsequent reaction of the crude fatty N-alkyl amide product formed by the process or (preferably) before. It is therefore preferred that the glycerol product and fatty N-alkyl amide be separated prior to any subsequent reaction of the amide or the glycerol formed.

The glycerol may be removed by extraction, centrifugation or other suitable means compatible with the final fatty N-alkyl amide. The removal may be conducted at the final reaction temperature or at a temperature where advantage can be taken of the differences in the physical properties of the glycerol and the fatty N-alkyl amide product. The process of the present invention allows for both chemical as well as physical methods of isolation due to the fact that there is a high conversion rate to the desired fatty N-alkyl amide. Since no solvent or catalyst is necessary to complete the reaction, such materials are not present to encumber the separation of the two reaction products.

GC Analysis Method. This method is applicable to the determination of the relative content of glycerol, fatty N-alkyl amides, mono-glycerides, di-glycerides, triglycerides, fatty acids, and amine reactants in reaction samples.

The components listed above are separated, after silylation, by temperature programmed GC on a 15 m DB1 column. A cool on-column injector is used and detection is by FID. Quantitation is performed using a $C_{12}$ fatty acid internal standard. The materials containing active hydrogens are derivatized with a 3:1:9:1 mixture of HMDS:TMCS:Pyridine:BSA.

| Chemicals: | |
|---|---|
| Pyridine, low water | J. T. Baker |
| TMCS, Trimethylchlorosilane | Pierce |
| HMDS, Hexamethyldisilizane | Pierce |
| BSA, N,O-bis(trimethylsilyl)trifluoroacetamide | Pierce |
| Lauric Acid, 99.5% | Aldrich |
| Equipment: | |
| Hewlett Packard 5890 GC | Hewlett Packard |
| On-column injection | |
| flame ionization detector | |
| Column: | |
| 15 m, DB-1, | J & W Scientific |
| 0.25 mm ID, | |
| 0.25 µm film | |
| Retention Gap: | |
| 1 m, 0.53 mm ID | Restek |

Procedure:

1. Internal Standard/Derivatization solution Preparation:

Prepare a 1400 ppm solution of the lauric acid in pyridine. Combine 7 parts of this solution with 2 parts of additional pyridine, 3 parts HMDS, 1 part TMCS, and 3 parts BSA. The resulting solution will provide the required 3:1:9:1 derivatization solution with 700 ppm of lauric acid internal standard. This internal standard/derivatization solution will be used in the preparation of all calibration standards and unknowns. This solution should be made fresh daily.

2. Calibration Standards Preparation:

Prepare standards for each component which bracket the levels expected in the unknown samples. Each sample should also be made containing 700 ppm of the lauric acid internal standard. For example, to prepare a 900 ppm calibration standard for oleic acid:

Weigh 4.5 mg of oleic acid into a 5 mL volumetric flask. Next, dilute to mark with the combined internal standard/derivatization solution. Mix well. Transfer ca. 1 mL of the sample to a GC vial. Cap and place vial in heated block at 80° C. for 40 minutes. The sample is now ready to be GC'ed.

3. Unknown Sample Preparation:

Weigh 5.0 mg of sample into a 5 mL volumetric flask. Dilute to mark with combined internal standard/derivatization solution. Mix well and transfer ca. 1 mL to a GC vial. Cap and heat for 40 minutes at 80° C. The sample is now ready to be GC'ed.

4. Instrument Settings.

Inlet Temperature: 60° C.

Detector Temperature: 340° C.

| Level | Rate | Temp | Time |
|---|---|---|---|
| Initial | — | 60° C. | 1.0 min. |
| Level 1 | 10° C. min. | 160° C. | 0.0 min. |
| Level 2 | 7° C. min. | 325° C. | 10.0 min. |
| Level 3 | 30° C. min. | 340° C. | 10.0 min. |

Total Run Time: 55.07 minutes

5. Approximate Retention Times:

| Component | Approximate RT (min.) |
|---|---|
| Glycerol | 6.5 |
| C18:1 N-methyl Amide | 18.9 |
| C16:1 Fatty Acid | 21.0 |
| C18:1 Fatty Acid | 23.6 |
| C18:0 Fatty Acid | 24.0 |

6. Calculation of $R_f$s for Calibration. After chromatographing each calibration standard, compile the areas for the compound and internal standard for each run. Calculate the $R_f$ as follows:

$$R_f = \frac{\text{Area Compound}}{\text{Conc. Compound}} * \frac{\text{Conc. Internal Standard}}{\text{Area Internal Standard}}$$

Concentration is in units of ppm. Calculate an average $R_f$ for each compound using the multiple calibrations standards which were run.

7. Calculation of Weight Percent. After running the unknown sample, determine the peak areas for each component plus the internal standard. Using the $R_f$ for a given component, calculate the weight percent as follows:

First, calculate the conc. of the component in the injected sample:

$$\text{Conc. Compound} = \frac{\text{Area Compound}}{R_f} * \frac{\text{Conc. Internal Standard}}{\text{Area Internal Standard}}$$

Finally, calculate the weight percent:

$$\text{Weight Percent Compound} = \frac{(\text{Conc. Compound, ppm}) * V_c}{W_c} * 100\%$$

Where,
$V_c$=Volume of flask in which unknown sample was prepared (in L)
$W_c$=Weight of sample weighed into flask (in mg)

The following examples further illustrate the present invention, but so not limit the scope of the invention.

EXAMPLE I

Synthesis of N-methyl oleoylamide

Charge to a pre-cooled (−780° C.) 500 mL glass autoclave liner containing 62.21 gm of high oleoyl sunflower seed oil under efficient nitrogen blanketing, 8.7 gm of methyl amine. Seal the liner, pressurize to 700–1000 psi $N_2$, begin rocking and heat to 100° C. for 24 hrs. Cool and remove the excess methyl amine in vacuo. After standing, separate the crystalline fatty N-alkyl amide by suction filtration. An alternative work-up suitable to this example allows the formulator to add sufficient hexane once the reaction has sufficiently cooled and to decant the fatty N-alkyl amide containing hexane phase from the glycerol.

EXAMPLE II

Synthesis of N-butyl lauroylamide

Charge to a 2000 mL 3-neck round bottom flask equipped with an efficient overhead mechanical stirrer, a nitrogen gas inlet tube and a reflux condenser 885 gm of CRISCO® oil and 400 gm of n-butyl amine. Heat the mixture to 125° C. with efficient stirring under a continuous blanket of nitrogen for 12 hrs. Cool and remove the unreacted butyl amine in vacuo and collect the N-butyl lauroylamide/glycerol product mixture or separate these products using standard separation techniques.

EXAMPLE III

Synthesis of N-methyl oleoylamide

Charge to a 2000 mL Parr hydrogenation vessel 1300 gm of canola oil (alkali refined, degummed and bleached) and G-95D® nickel catalyst (approx. 0.02% as nickel). Hydrogenate at a maximum of 45 psig $H_2$ at 160° C. with continuous (600 rpm) agitation until the oleic acid content as measured by G.C. is at least 70%. De-gas and remove the catalyst, cool the oil, transfer to a 2 gallon stainless steel stirred autoclave and sparge under nitrogen. Evacuate the autoclave until the vacuum reaches less than 1 mm Hg. Condense in a separate stainless steel vessel that is connected to the autoclave via stainless steel tubing a large stoichiometric excess of methyl amine. This container serves as a convenient reservoir. Allow the methyl amine to fill the head space of the autoclave until equilibrium is obtained between the two vessels. Heat the autoclave with good stirring to 100° C. and monitor the head space pressure. Periodically add methyl amine as the amine reactant is used up and the autoclave head space pressure drops. Once the reaction is complete, cool the autoclave, vent with nitrogen gas and remove the excess methyl amine in vacuo. Filter by suction the slurry while still warm and continue suction until the glycerol is removed. The resulting fatty N-alkyl amide product is sufficiently pure for direct use in chemical applications.

The above example is applicable for any glyceride feedstock, whether the hydrogenation step is included or not. Other amine reactants, including ammonia, are suited to this procedure whether gaseous or liquid, since the amine reactant can be efficiently introduced by nitrogen pressurization of the holding vessel.

What is claimed is:

1. A method for preparing N-methyl oleoyl amide consisting essentially of the steps of:

(a) reacting under anhydrous conditions a glyceride, wherein at least 40% of the fatty acid moieties of the glyceride are oleoyl, and methyl amine to form N-methyl oleoylamide; and (b) removing the glycerol formed by the reaction of step (a).

2. The method according to claim 1 wherein the reaction step (a) comprises less than about 0.1% water and is solventless.

\* \* \* \* \*